United States Patent [19]

Kawai et al.

[11] Patent Number: 5,433,830
[45] Date of Patent: Jul. 18, 1995

[54] METHOD OF ACTIVATING ZIRCONIA OXYGEN SENSOR

[75] Inventors: Takeshi Kawai; Nobuhiro Hayakawa; Tessho Yamada, all of Aichi, Japan

[73] Assignee: NGK Spark Plug Co., Ltd., Aichi, Japan

[21] Appl. No.: 186,650

[22] Filed: Jan. 26, 1994

[30] Foreign Application Priority Data

Dec. 29, 1993 [JP] Japan ............................ 5-349589

[51] Int. Cl.⁶ ........................................... G01N 27/26
[52] U.S. Cl. ........................ 204/153.18; 204/153.1; 204/425
[58] Field of Search ............... 204/402, 424, 425, 426, 204/427, 421, 153.1, 153.18, 130

[56] References Cited

U.S. PATENT DOCUMENTS 4,702,816 10/1987 Hashimoto et al. ............... 204/425
5,130,002 7/1992 Murase et al. ..................... 204/424
5,281,313 1/1994 Visser et al. ....................... 204/425

*Primary Examiner*—John Niebling
*Assistant Examiner*—Bruce F. Bell
*Attorney, Agent, or Firm*—Sughrue, Mion, Zinn, Macpeak & Seas

[57] ABSTRACT

Activation treatment for a zirconia oxygen sensor is performed by applying alternately a treating voltage, which can make an oxygen partial pressure at the electrode-zirconia interface of a sensor equal to or higher than a critical oxygen partial pressure value ($10^{-34}$ atm) not to cause blackening, between a pair of electrodes of the sensor at temperatures of 500° to 800° C. As a result, the treatment current flowing through the sensor can always be held below the critical level, whereby the sensor can be activated without causing blackening and other physical structural changes to occur in the zirconia sensing element. If the sensor is to be used in an A/F ratio control or the like on an internal combustion engine, it can be rendered active at all times by the activation treatment during or before or after the control.

7 Claims, 7 Drawing Sheets

METHOD OF ACTIVATING ZIRCONIA OXYGEN SENSOR

BACKGROUND OF THE INVENTION

The present invention relates to a method of activating a zirconia oxygen sensor which detects the oxygen concentration of an ambient atmosphere by means of a zirconia element that has a porous electrode formed on both sides of an oxygen ion conductive solid zirconia electrolyte.

The sensing element used in zirconia oxygen sensors is produced through a process that comprises the steps of forming a plate of sensor body from partially stabilized zirconia, fully stabilized zirconia, etc., attaching a platinum or other metal electrode to both sides of the plate, and firing the assembly in a temperature-controlled furnace. The thus produced sensing element, as it emerges from the firing furnace, is not suitable for immediate use since its internal resistance has increased markedly due to the oxygen which binds to the electrodes. One of the conventional methods for solving this problem is taught in Japanese Patent Unexamined Publication No. Hei 3-156361 and it consists of causing an alternating current to flow between the electrodes of the fired sensing element, so that it is activated to have a lower internal resistance.

However, in order to reduce the internal resistance of the sensing element by this conventional approach of activation, the surface of the metal grains which form the electrodes must be rendered to have a fine-grained structure by supplying the zirconia oxygen sensor with an alternating current 1 to 5 times as large as the critical current. Although this method is capable of reducing the internal resistance of the sensing element, an undesired phenomenon called "blackening" takes place in the zirconia during the activation treatment, thereby deteriorating the endurance of the sensing element.

This problem is further discussed below. First, when an alternating current 1 to 5 times as large as the critical current is admitted to activate the sensing element as in the prior art, the concentration of oxygen at the zirconia-electrode interface becomes so low during the activation that the reaction $ZrO_2 \rightarrow Zr + O_2$ will occur on the surface of zirconia and the structure of the affected surface area is destroyed (occurrence of cracks) to become brittle. Thus, the surface of metal grains constituting the electrode is also finely grained. Since the brittle structure is black in color, this phenomenon is generally called "blackening".

When blackening occurs during the activation treatment, if it can be recognized after the treatment, it will not be a problem since one can check for its occurrence in subsequent steps such as inspection. In fact, however, in the conventional practice of activation treatment, in addition to the application of an alternating current, depending on the other conditions for performing the treatment such as a comparatively small treating current and a comparatively high treating temperature, the sign of blackening that once occurred during the activation treatment may disappear and cannot be effectively detected after the treatment; in this case, the defective sensing element will be used as a normal sensing element.

However, zirconia which once experienced blackening is deteriorated in its internal structure, so if one attempts to reactivate the sensor by performing periodic activation treatments during its service, the internal deterioration will progress and its endurance drops to shorten its useful life considerably.

Another reason for the failure to recognize the previous occurrence of blackening after the activation treatment may be explained as follows: not only just after the activation treatment but also during subsequent use, the oxygen in the ambient atmosphere will initiate the reaction $Zr + O_2 \rightarrow ZrO_2$ on the surface of zirconia which experienced blackening and, as a result, zirconia's surface which once turned black and brittle reverts to the initial white color.

SUMMARY OF THE INVENTION

The present invention has been accomplished under these circumstances and has an object to provide a method of activating a zirconia oxygen sensor by which the sensing element can be activated effectively without causing any physical structural changes such as blackening in zirconia in the process of the activation treatment.

According to the present invention, activation treatment for a zirconia oxygen sensor is performed by applying alternately a treating voltage, which can make an oxygen partial pressure at the electrode-zirconia interface of a sensor equal to or higher than a critical oxygen partial pressure value ($10^{-34}$ atm) not to cause blackening, between a pair of electrodes of the sensor at temperatures of 500° to 800° C. As a result, the treatment current flowing through the sensor can always be held below the critical level, whereby the sensor can be activated without causing blackening and other physical structural changes to occur in the zirconia sensing element. If the sensor is to be used in an A/F ratio control or the like on an internal combustion engine, it can be rendered active at all times by the activation treatment during or before or after the control.

DETAILED DESCRIPTION OF THE PREFERRED EMBODIMENTS

Preferred embodiments of the present invention will be described with reference to the accompanying drawings.

First, various aspects of the present invention will be described.

A first aspect of the present invention is a method of activating a zirconia oxygen sensor that is equipped with a sensing element which has at least one pair of porous electrodes formed on both sides of a plate of oxygen ion conductive solid zirconia electrolyte. The method is characterized in that a specified voltage of such magnitude that the oxygen partial pressure at the electrode-to-solid electrolyte interface of the sensing element is greater than the critical oxygen partial pressure at which the solid electrolyte blackening occurs, is applied alternately between the electrodes at a temperature of 500° to 800° C.

A second aspect of the present invention is a modification of the method for activating a zirconia oxygen sensor according to the first aspect. That is, a measuring device has a pair of porous electrodes formed on both sides of a plate of oxygen ion conductive solid zirconia electrolyte similarly to the sensing element to be activated in the first aspect of the present invention, and further has one of the two electrodes being substantially isolated hermetically from the ambient atmosphere. A dc current is applied between the pair of electrodes of the measuring device in a specified atmosphere for a sufficient period of time, with the isolated electrode being used as cathode, so as to measure the critical electromotive force generated by the sensing element in the specified atmosphere, and the voltage to be applied alternately between the electrodes of the sensing element is set on the basis of the thus measured critical electromotive force.

A third aspect of the present invention is a modification of the second aspect of the present invention. According to the third aspect, the critical oxygen partial pressure at the cathodic electrode is computed from both the critical electromotive force in the specified atmosphere as measured with the measuring device and the oxygen partial pressure of the ambient atmosphere at the time of the measurement, and the voltage to be applied alternately between the electrodes of the sensing element is set on the basis of the thus computed critical oxygen partial pressure.

A fourth aspect of the present invention is a modification of the third aspect of the present invention. According to the fourth aspect, if the ambient atmosphere in which the sensing element is to be placed during the activation treatment, is an oxygen containing combustion gas atmosphere that is produced by burning either atmospheric air or an air-fuel mixture having an air excess factor λ greater than one, the oxygen partial pressure is computed for thermodynamic equilibrium either in the ambient atmosphere or in an atmosphere having a lower oxygen concentration than the ambient atmosphere and, at the same time, the critical electromotive force is computed from the Nernst equation on the basis of both the thus computed oxygen partial pressure and the critical oxygen partial pressure as computed in the third aspect. The voltage to be applied alternately between the electrodes of the sensing element is set on the basis of the thus computed critical electromotive force.

A fifth aspect of the present invention is also a modification of the third aspect of the present invention. According to the fifth aspect, if the ambient atmosphere in which the sensing element is to be placed during the activation treatment, is an oxygen compound containing combustion gas atmosphere that is produced by burning an air-fuel mixture having an air excess factor λ equal to or smaller than one, the oxygen partial pressure is computed for thermodynamic equilibrium either in the ambient atmosphere or in an atmosphere having a lower oxygen compound concentration than the ambient atmosphere and, at the same time, the critical electromotive force is computed from the Nerst equation on the basis of both the thus computed oxygen partial pressure and the critical oxygen partial pressure as computed in the third aspect. The voltage to be applied alternately between the electrodes of the sensing element is set on the basis of the thus computed critical electromotive force.

A sixth aspect of the present invention is a modification of the first aspect of the present invention. According to the sixth aspect, a dc voltage is applied to a sensing element having the same structure as the actual sensing element under the conditions for the activation treatment for a sufficient period of time so as to determine the critical voltage at which the oxygen partial pressure at the electrode-to-solid electrolyte interface of the sensing element becomes equal to the critical oxygen partial pressure at which the solid electrolyte blackens. The voltage to be applied alternately between the electrodes of the sensing element during the activation treatment is set at a smaller value than the critical voltage.

A seventh aspect of the present invention is a modification of any of the previous aspects of the present invention. According to the seventh aspect, the voltage to be applied alternately between the electrodes of the sensing element is at least 0.4 volts.

A eighth aspect of the present invention is a modification of any of the previous aspect of the present invention. According to the eighth aspect, the specified voltage is applied between the electrodes of the sensing element at a frequency not higher than 0.5 Hz.

A ninth aspect of the present invention is a modification of any of the previous aspects of the present invention. According to the ninth aspect, the activation treatment is performed on the zirconia oxygen sensor during or prior to or after its operation either periodically or as required.

The operations and effects of the various aspects of the present invention will next be described.

When a voltage is applied between the electrodes of the sensing element, a current flows through the element and oxygen flows in a direction that opposes the current flow, namely, from the lower-potential electrode (cathode) towards the higher-potential electrode (positive electrode).

As more current flows through the sensing element, it is no longer possible to admit oxygen from the cathode side and the oxygen partial pressure at the zirconia-electrode interface (this interface is hereunder referred to as the "three-phase interface") on the cathode side drops markedly, causing the reaction $ZrO_Z \rightarrow Zr + O_2$ to proceed at the surface of zirconia on the cathode side, whereby blackening occurs in zirconia.

Hence, in accordance with the activation method of the present invention, a current is applied to the sensing element alternately so as to lower its internal resistance and, at the same time, care is taken to insure that the oxygen partial pressure at the three-phase interface will not, at any time of the current impression, become equal to or lower than the critical oxygen partial pressure at which blackening occurs in zirconia.

Thus, in the basic method of activating a zirconia oxygen sensor according the the first aspect of the present invention, a specified voltage of such a magnitude that the oxygen partial pressure at the electrode-to-solid electrolyte interface of the sensing element is greater than the critical oxygen partial pressure at which the solid electrolyte (i.e., zirconia) blackens, is applied alternately between the electrodes of the sensing element at a temperature of 500° to 800° C., whereby it is assured to prevent the occurrence of blackening during the activation treatment.

As already mentioned in connection with the description of the prior art, according to the conventional practice for lowering the internal resistance of the sensing element, a sufficient current to render the electrode surfaces fine-grained (i.e., 1 to 5 times as large as the critical current) has been supplied. Thus, the activation treatment by this method cannot be performed without causing blackening to occur in zirconia. On the other hand, the present invention performs the intended activation treatment by applying voltage alternately to the sensing element in a limited manner as described above in order to ensure that blackening will not occur in zirconia at any time in the process of the treatment.

Hence, according to the present invention, even a comparatively slight level of blackening that would disappear after the end of the activation treatment, is not allowed to occur during the treatment, and the treatment can be accomplished successfully to enhance the durability of the sensing element.

It should be noted here that the critical oxygen partial pressure at which blackening occurs in zirconia cannot be determined uniquely since it depends on various factors such as the construction of the sensing element, its material and the temperature condition under which it is used. Nevertheless, rough estimation is possible on the basis of experimentation and the like and, hence, if one assumes the critical oxygen partial pressure from the estimated value, the treating voltage can be set by the following procedure.

That is, an electromotive force EMF develops between the electrodes of the sensing element in accordance with the oxygen concentration at the three-phase interface on each electrode side, and this electromotive force may be expressed by the following equation (1) which is well known as the Nornst equation:

$$EMF = (RT/nF) \times \ln(PO1/PO2) \quad (1)$$

where R is the gas constant; T is the absolute temperature; n is the valence number of oxygen; F is the Faraday constant; PO1 is the oxygen partial pressure at the three-phase interface on one electrode side; and PO2 is the oxygen partial pressure at the three-phase interface on the other electrode side. If the current flowing through the sensing element and the internal resistance of the element are written as Ip and Ri, respectively, then the voltage to be applied between the electrodes, Vp, can be expressed as:

$$Vp = Ip \times Ri + EMF \quad (2)$$

Therefore, by substituting into equation (1) the assumed critical oxygen partial pressure PO2, the oxygen partial pressure PO1 in the ambient atmosphere during the activation treatment and the absolute temperature T of the sensing element, one can determine the critical electromotive force EMF that causes blackening to occur in zirconia; one may then set the treating voltage in such a way that the applied voltage Vp satisfies the following relation (3):

$$Vp < \text{critical EMF} + Ip \times Ri \quad (3)$$

In the first aspect, the temperature range for the activation treatment to be performed is set as 500° to 800° C. and this is because the intended result of the treatment by the application of an alternating voltage is attained within the specified range. This numerical range is determined by the temperature experiment to be described hereinafter.

It is worth mention here that the critical electromotive force EMF can be measured with extremely high precision by experimentation without using the assumed value of the critical oxygen partial pressure PO2.

To this end, the following procedure may be taken: first, one of the two electrodes on the sensing element is isolated from the ambient atmosphere, and a dc voltage is applied between the electrodes, with the isolated electrode used as cathode, for a sufficient period of time until blackening occurs in zirconia. Then, the applied voltage Vp, which is equal to the critical electromotive force EMF, is measured. In other words, the current Ip that flows through the experimental setup in which one of the two electrodes is isolated from the ambient atmosphere, will converge to zero unless blackening occurs in the sensing zirconia element; hence, the applied voltage Vp is equal to the limiting electromotive force EMF, thereby enabling the operator to know the most exact value of EMF.

Accordingly, in the method of activating a zirconia oxygen sensor according to the second aspect of the present invention, the critical electromotive force EMF is measured with a measuring sensing element (measuring device) in which one of the two electrodes is isolated from the ambient atmosphere, and the treating voltage to be applied is set on the basis of the thus measured critical electromotive force EMF.

Thus, according to the method of the second aspect, the treating voltage to be applied can be set from the critical electromotive force EMF which causes blackening to occur actually in zirconia and, therefore, the possible occurrence of blackening during the activation treatment can be prevented more positively.

Next, when the critical electromotive force EMF which causes blackening to occur in such zirconia, is not measured under the conditions (atmosphere) in which the activation treatment is actually performed, this critical electromotive force value can not be used.

However, the measured EMF can be described by equation (1). Accordingly, if the EMF is measured in an atmosphere of known oxygen concentration, the oxygen partial pressure at the three-phase interface on the open (not isolated) positive electrode side, PO1, can be correctly given by using the known oxygen concentration. Hence, by substituting the values of both the oxygen partial pressure PO1 and the measured EMF into equation (1), one can determine the critical oxygen partial pressure PO2 at which zirconia blackens.

Accordingly, in the method of activating a zirconia oxygen sensor according to the third aspect of the present invention, the critical oxygen partial pressure at the cathodic electrode has been computed from both the critical electromotive force in an atmosphere of a known oxygen partial pressure as measured with the measuring device and the oxygen partial pressure during that measurement, and the treating voltage to be applied alternately between the electrodes of the sensing element is set on the basis of the thus computed critical oxygen partial pressure without obtaining the critical electromotive force using the measuring device at every time.

That is, according to the third aspect, the activation treatment voltage not to cause blackening can be set by calculation even for the ambient atmosphere in which the critical electromotive force EMF is not measured at every time with the measuring device having one element isolated from the ambient atmosphere.

In the above-described case where the critical oxygen partial pressure is determined from the measured value of EMF, it is also necessary that the critical electromotive force EMF in the ambient atmosphere in which the activation treatment is to be performed, should be determined from the thus determined critical oxygen partial pressure in order to set the treating voltage in such a way as to satisfy the relation (3).

Therefore, according to the fourth aspect of the present invention, when the ambient atmosphere of the sensing element to be activated is an atmospheric air or an oxygen containing combustion gas atmosphere (so-called "fuel-lean" atmosphere) that is produced by burning an air-fuel mixture having an air excess factor $\lambda$ greater than one ($\lambda > 1$), the method of the third aspect is performed such that the oxygen partial pressure is computed for thermodynamic equilibrium either in the ambient atmosphere or in an atmosphere having a lower oxygen concentration than the ambient atmosphere and, at the same time, the critical electromotive force in the fuel-lean atmosphere where the activation treatment is to be performed, is computed from equation (1) (the Nernst equation) on the basis of both the thus computed oxygen partial pressure and the critical oxygen partial pressure as computed by the method of the third aspect. The voltage to be applied alternately between the electrodes of the sensing element is set on the basis of the thus computed critical electromotive force.

On the other hand, according to the fifth aspect of the present invention, when the ambient atmosphere of the sensing element to be activated is an oxygen compound containing combustion gas atmosphere ("fuel-rich" atmosphere) that is produced by burning an air-fuel mixture having an air excess factor equal to or smaller than one ($\lambda \leq 1$), the method of the third aspect is performed such that the oxygen partial pressure is computed for thermodynamic equilibrium either in the ambient atmosphere or in an atmosphere (richer atmosphere) having a lower oxygen compound concentration than the ambient atmosphere and, at the same time, the critical electromotive force in the fuel-rich atmosphere where the activation treatment is to be performed, is computed from equation (1) (the Nernst equation) on the basis of both the thus computed oxygen partial pressure and the critical oxygen partial pressure as computed by the method of the third aspect. The voltage to be applied alternately between the electrodes of the sensing element is set on the basis of the thus computed critical electromotive force.

Thus, in accordance with the methods of the fourth and fifth aspects of the present invention, the treating voltage that is adaptive to the ambient atmosphere in which the activation treatment is to be performed can be set to values safely using the critical oxygen partial pressure of the sensing element that has been determined by the method of the third aspect.

In the methods of the second to fifth aspects, the critical electromotive force which causes blackening to occur in zirconia is measured with a separate measuring device, and the treating voltage is set on the basis of the thus measure value of the critical electromotive force. It should, however, be noted that the treating voltage that will not cause blackening to occur in zirconia can also be measured by applying a dc voltage to the sensing element.

That is, when an alternating current is applied to the sensing element for its activation, the applied voltage on each electrode will change cyclically to assume either a positive or a negative value; therefore, even if blackening occurs in zirconia during the treatment, it does not progress to such an extent that it persists after the end of the treatment, but instead it will soon disappear. In order to insure that blackening will not occur at any time in the process of the activation treatment, one only need set a voltage value that will not cause blackening to occur in zirconia even if the voltage is applied to the sensing element in one direction for a certain period of time. To determine this voltage value, a dc voltage is supplied to the sensing element for a sufficient period of time until blackening occurs and then measure the voltage at this critical time.

Accordingly, in the method of the sixth aspect of the present invention, a dc voltage is applied to a sensing element having the same structure as the actual sensor under the conditions for the performance of the activation treatment, and the critical voltage at which the oxygen partial pressure at the electrode-to-solid electrolyte interface of the sensing element becomes equal to the critical oxygen partial pressure at which zirconia blackens, is obtained. A voltage smaller than this critical voltage is set as the voltage to be applied alternately between the electrodes of the sensing element for the activation treatment.

Thus, the method of the sixth aspect is also capable of activating the sensing element in a zirconia oxygen sensor to lower its internal resistance without blackening, thereby enhancing the durability of the sensor.

In the methods of the first to sixth aspects, the internal resistance of the sensing element is lowered by applying a specified voltage alternately between the electrodes of the element. If, in this case, the treating voltage to be applied is unduly low, no satisfactory results can be attained. Therefore, the treating voltage to be applied is preferably set at 0.4 volts or higher in the seventh aspect of the present invention.

It should also be noted that if the period of the treating voltage to be applied alternately between the electrodes of the sensing element is unduly short, no current will effectively flow through the sensing element even if it is supplied with the treating voltage and, therefore, no satisfactory results can be attained. Thus, the period of the treating voltage to be applied alternately between the electrodes of the sensing element, in other words, the frequency of that treating voltage, is preferably adjusted to 0.5 Hz or below in the eighth aspect of the present invention.

The lower limit of the treating voltage (0.4 V) and the upper limit of its frequency (0.5 Hz) which are according to seventh and eights aspects, respectively, were determined by the associated experiments to be described hereinafter.

As already mentioned in connection with the prior art, zirconia oxygen sensors just emerging from the firing furnace have their internal resistance elevated on account of the oxygen binding to the electrode surfaces. Hence, they are conventionally subjected to the activation treatment just after their production (i.e., before delivery to their customers).

However, the internal resistance of the activated zirconia oxygen sensors tends to increase again as a result of prolonged use. This tendency becomes pronounced if the sensors are used at comparatively low temperatures for a prolonged period, with a voltage being applied in such a direction that oxygen ions are admitted from the electrode side that is exposed to an oxidizing atmosphere. This phenomenon would probably be caused by the adsorption of gases or depolarization (distortion), and it can cause a serious problem if the zirconia oxygen sensor is used as an A/F ratio sensor for controlling the A/F ratio of an internal combustion engine to be adjusted to the desired level such as the stoichiometric, because the target of control will deviate in response to the increasing internal resistance.

Accordingly, in the method of the ninth aspect of the present invention, the sensor is not subjected to the activation treatment only once just after its production but it is also treated during or prior to or after its operation either periodically or as required.

Thus, according to the ninth aspect, any deterioration in the characteristics of the zirconia oxygen sensor that can occur as a result of its use is effectively prevented and yet the sensor can always be held in active state, thereby contributing to a higher precision in control operations such as the control over A/F ratio using the zirconia oxygen sensor.

The preferred embodiments of the present invention will be described below more specifically with reference to the accompanying drawings.

Figure 1:
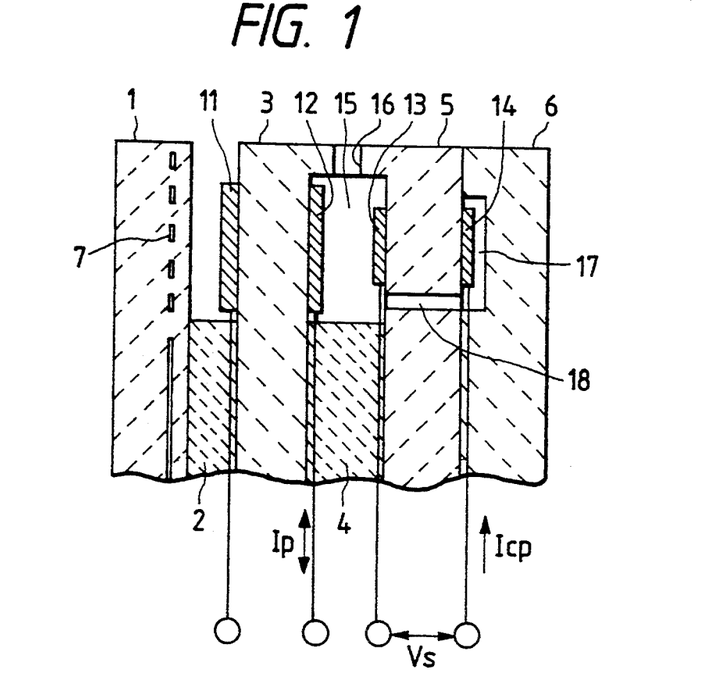
FIG. 1 is a simplified sectional view showing the construction of an A/F ratio sensor that is to be activated by an embodiment of the present invention.

FIG. 1 is a simplified sectional view showing the construction of an A/F ratio sensor, which uses two sensing elements (sensor cells) of zirconia oxygen sensor, for monitoring the A/F ratio of an air-fuel mixture fed to an internal combustion engine on the basis of compositional analysis of the exhaust from the engine.

As shown in FIG. 1, the sensor comprises a heater plate 1, a spacer 2, a pump cell 3, a spacer 4, an electromotive force generating cell 5 and a shield plate 6 that are stacked in an assembly form. A heater 7 is embedded in the plate 1 and by impressing a current through the heater 7 with a control circuit (not shown), the pump cell 3 and the electromotive force generating cell 5 which are sensing elements can be maintained at a temperature of about 800° C. The spacers 2 and 4 are each an electric insulator made of aluminum.

The pump cell 3 is formed of stabilized or partially stabilized zirconia which is an oxygen ion conductive solid electrolyte material. The pump cell 3 has porous platinum electrodes 11 and 12 provided on the front and back sides, respectively. The porous electrode 11 faces outward so it is exposed directly to an atmosphere filled with the gas to be analysed.

Similarly to the pump cell 3, the electromotive force generating cell 5 is formed of stabilized or partially stabilized zirconia and has porous platinum electrodes 13 and 14 provided on the front and back sides, respectively.

Between the pump cell 3 and the electromotive force generating cell 5, there is formed a diffusing compartment 15 that communicates with the gas atmosphere under analysis via a gas diffusion limiting portion 16 that is either a small hole or which is formed by filling a small hole with a porous material.

An internal reference oxygen compartment 17 is formed at the back of the electromotive force generating cell 5 and this compartment communicates with the diffusing compartment 15 via a leakage resisting portion 18 that is either a small hole or which is formed by filling a small hole with a porous material.

The thus constructed A/F ratio sensor is drive controlled by a drive circuit (not shown) in the manner described below.

The control circuit supplies at all times a constant current Icp to the electromotive force generating cell 5 so that oxygen in the diffusing compartment 15 is pumped into the internal reference oxygen compartment 17, whereby the oxygen partial pressure in the compartment 17 is controlled at a specified level, while the control circuit detects the electromotive force Vs which the cell 5 generates in correspondance to the ratio between the oxygen partial pressure in the internal reference oxygen compartment 17 and that in the diffusing compartment 15. In order to insure that the electromotive force Vs is always held constant, namely, the oxygen partial pressure in the diffusing compartment 15 is held constant, the control circuit performs two-way control over the current Ip flowing into the pump cell 3, so that oxygen will be transferred from the diffusing compartment 15 into the gaseous atmosphere under analysis or vice versa (hence, the flow of oxygen is bidirectional). The thus controlled current Ip is used as an index for detecting the A/F ratio of the air-fuel mixture fed to the internal combustion engine.

In the electromotive force generating cell 5 of the A/F ratio sensor under discussion, voltage is kept applied between the electrodes 13 and 14 in such a way that oxygen ions are always transferred from the electrode 13 to the electrode 14. Therefore, if the cell is operated for a prolonged time, its internal resistance will increase probably because oxygen is adsorbed on the electrode 14.

If the A/F ratio sensor is to be used for controlling the A/F ratio of the internal combustion engine so that the air excess factor ($\lambda$) of the gaseous atmosphere being analyzed remains greater than one for a long time, voltage is also applied to the pump cell 3 in such a way that oxygen ions are transferred from the diffusing compartment 15 into the gaseous atmosphere under analysis. As a result, the internal resistance of the pump cell will also rise probably because of oxygen adsorption on the electrode 11.

Under the circumstances, the A/F ratio sensor of the embodiment under consideration is subjected to the activation treatment in accordance with the present invention not only after the firing of the sensor cells 3 and 5 but also during or before and after the performance of A/F ratio control on the internal combustion engine, whereby both sensor cells 3 and 5 can advantageously be prevented from the above-described characteristic deterioration.

On the pages that follow, the activation treatment which is to be conducted in order to lower the internal resistance of the A/F ratio sensor of the embodiment under consideration will be described.

The activation treatment is performed by applying an alternating voltage between the electrodes of each of the sensor cells 3 and 5. However, it should be mentioned that if the applied voltage is excessive, blackening will occur in the cell composing zirconia during the treatment and even if it disappears after the end of the treatment on account of reoxidation of the affected area, that area will deteriorate.

To solve this problem, according to this embodiment, the alternating voltage to be applied between the electrodes of each of the sensor cells 3 and 5 at the activation treatment is set as described below.

First, a flat sheet of zirconia (indicated by Z in FIG. 2) was prepared from the same material by the same process as the sensor cells 3 and 5. Then, porous platinum electrodes 100 and 200 were formed on the front and back sides of the zirconia sheet Z using the same material and the same method as in the case of the sensor cells 3 and 5, except that the platinum electrode 200 was equipped with a cover C so that it was substantially isolated from atmospheric air. In this way, a measuring cell 30 was constructed.

Figure 2:
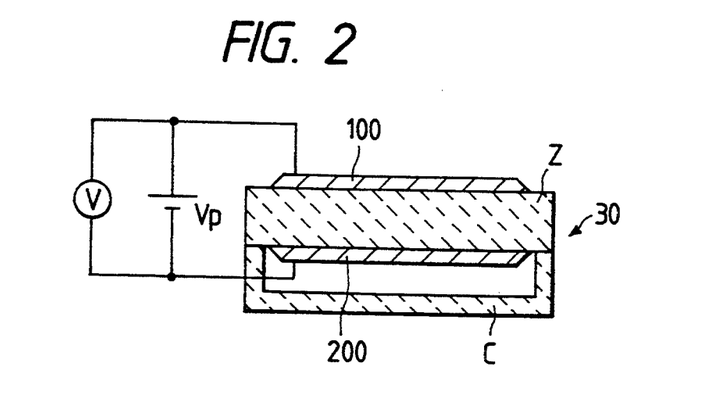
FIG. 2 is a simplified sectional view showing the construction of a measuring device that may be used to determine the critical electromotive force which is a threshold for the occurrence of blackening.

In the next step, a dc voltage Vp was applied between the Pt electrodes 100 and 200, with the latter being used as cathode, at 727° C. (1,000° K.) in atmospheric air until zirconia blackened, and the critical voltage that caused blackening was measured. The dc voltage Vp was applied for 3 h, which was sufficient to verify the occurrence of blackening in zirconia.

As a result, the critical voltage that caused the measuring cell 30 to blacken at 727° C. in atmospheric air was found to be greater than 1.7 volts but smaller that 2.0 volts.

It should be remembered here that the applied voltage Vp is expressed by equation (2). The electromotive force EMF which is generated in the measuring cell 30 upon voltage application is determined by the Nernst equation (1). If the temperature condition for measurement of the critical voltage is 727° C. (1,000° K.), one may substitute this value into the Nernst equation and calculate the electromotive force EMF as follows:

$$EMF = 50 \times \log (P01/P02) \quad (4)$$

Since the platinum electrode 200 in the measuring cell 30 is completely isolated from atmospheric air by means of the cover C, the current Ip will converge to zero unless zirconia ($ZrO_2$) blackens.

From equations (2) and (4), the applied voltage Vp is given by:

$$\begin{aligned}
Vp[V] \times 1,000 &= EMF[mV] \\
&= (RT/nF) \times \ln(P01/P02) \\
&= 50 \times \log(P01/P02)
\end{aligned} \quad (5)$$

Since atmospheric air has an oxygen partial pressure of about 0.2 atm, the oxygen partial pressure at the three-phase interface toward the Pt electrode 100, P01, during the measurement of the critical voltage is also about 0.2 atm.

Hence, substituting 0.2 atm and the voltage 1.7 V into the respective terms P01 and Vp of equation (5), one can calculate the oxygen partial pressure at the three-phase interface toward the Pt electrode 200, P02, to be $10^{-34.7}$ atm.

One can, therefore, see that the sensor cells 3 and 5 in the A/F ratio sensor of the embodiment under consideration will not blacken if the oxygen partial pressure at the three-phase interface toward the electrode that serves as cathode during voltage application is at least $10^{-34}$ atm as the safe critical value.

One can also see from the above results of measurement that when activating the sensor cells 3 and 5 in atmospheric air, the occurrence of blackening in those cells can be prevented by insuring that they will not generate an electromotive force greater than 1.7 volts.

Therefore, one may safely conclude that in view of equation (3), the treating voltage (alternating voltage) which is to be applied to activate the sensor cells 3 and 5 in atmospheric air, need be so set as to satisfy the relation $Vp \leq 1.7 + Ip \times Ri[V]$. In the embodiment under consideration, the treating voltage to be used when performing the activation treatment on the sensor cells 3 and 5 in atmospheric air was set at 1.5 volts. By applying this value of voltage alternately between the electrodes of each sensor cell, effective activation could be accomplished.

Thus, the treating voltage to be applied when the A/F ratio sensor mounted in the exhaust system of an internal combustion engine is activated either in atmospheric air or in an atmosphere equivalent to the atmospheric air that occurs typically before the engine is started after an adequately long stop or while engine brake is on without fuel supply, can be set on the basis of the result of measurement of the critical voltage that was conducted in the manner described above using the measuring cell 30. However, if it is necessary to perform the activation treatment during engine operation, the treating voltage applicable to the treatment in atmospheric air cannot be used as such since both sensor cells 3 and 5 are exposed to the exhaust from the engine.

It should also be noted that the exhaust from the normally running engine is highly dependent on the state of engine operation and can change from the "fuel-lean" atmosphere (the state of the oxygen-rich exhaust which is discharged while the engine is running with an air-fuel mixture whose air excess factor λ is greater than one) to the "fuel-rich" atmosphere (the state of the oxygen-lean exhaust which is discharged while the engine is running with an air-fuel mixture whose air excess factor λ is equal to or smaller than one). Therefore, when performing the activation treatment during engine operation, the treatment voltage has to be set in such a way that blackening will not occur in the sensor cells 3 and 5, and the activation treatment is effectively performed even if the treatment is conducted in the fuel-rich atmosphere where blackening is most likely to occur in those cells.

Under the circumstances, the treating voltage to be applied in the embodiment when the A/F ratio sensor mounted in the exhaust system of an internal combustion engine was activated during engine operation, was set by the following procedures in order to insure the performance of the desired treatment without causing blackening in the sensor cells 3 and 5, assuming that a minimum air excess factor for the case where the fuel ratio of the air-fuel mixture becomes the highest during idling, acceleration, running under high load, etc., is $\lambda = 0.8$.

First, a dc voltage was applied between the electrodes of each of the sensor cells 3 and 5 while they were exposed to an oxygen-lean and fuel-rich atmosphere. As a result, the oxygen compounds in the fuel-rich atmosphere experienced dissociation of oxygen at the three-phase interface on the cathodic electrode side, whereupon a current flowed into the sensor cells 3 and 5.

Stated more specifically, the exhaust from the internal combustion engine contains oxygen compounds such as $H_2O$ and $CO_2$, so even if the exhaust is substantially free of oxygen, such oxygen compounds present in it will experience the dissociation of oxygen, thus permitting a current to flow into the sensor cells 3 and 5.

Since the mechanism of oxygen dissociation is generally the same with $H_2O$ and $CO_2$, the following discussion of a current flowing into the sensor cells assumes that it is initiated by the dissociation of oxygen in $H_2O$.

It should first be mentioned that the equilibrium constant of $H_2O$ at the absolute temperature 1,000K. is given by:

$$(PH_2 \times PO_2^{\frac{1}{2}})/PH_2O = 8.73 \times 10^{-11}$$

Assuming the $H_2$ combustion system as a model and also assuming that the air excess factor $\lambda$ of the air-fuel mixture to be supplied to this combustion system is 0.8 which is a minimum value for the internal combustion engine, the combustion of the air-fuel mixture will proceed as follows:

$$H_2 + 0.4 \cdot O_2 \rightarrow 0.8 H_2O + 0.2 H_2$$

On this occasion, oxygen having the partial pressure $PO_2$ will be dissociated from $H_2O$ in accordance with its equilibrium constant but this is so smaller than $H_2O$ and $H_2$ that it can be neglected to yield:

$$(0.2 \times PO_2^{\frac{1}{2}})/0.8 = 8.73 \times 10^{-11}$$

Therefore, the oxygen partial pressure toward the electrode 100, PO1, which is exposed to the reducing atmosphere is given by:

$$PO1 = PO_2 = (3.49 \times 10^{-11})^2 = 1.2 \times 10^{-21}$$

Hence, the critical voltage for the occurrence of blackening in the exhaust (fuel-rich atmosphere) having the air excess factor $\lambda = 0.8$ is calculated from equation (5) as:

$$EMF = 50 \log (10^{-20}/10^{-34.7}) = 0.735$$

Thus, one can see that when activating the sensor cells 3 and 5 during engine operation, the occurrence of blackening in those cells can be prevented by insuring that they will not generate an electromotive force greater than 0.7 volts.

Therefore, one may safely conclude that in view of equation (3), the treating voltage (alternating voltage) which is to be applied to activate the sensor cells 3 and 5 in the rich atmosphere need be so set as to satisfy the relation $Vp \leq 0.7 + Ip \times Ri$ [V].

Under the air excess factor $\lambda = 0.8$, and the temperature 727° C., the critical electrimotive force EMF was directly measured by using the measuring device. The results were 0.9–1.1 V.

In the embodiment under consideration, the treating voltage to be used when performing the activation treatment on the A/F ratio sensor mounted on the exhaust system in the internal combustion engine during its operation under the condition of $\lambda \leq 1$ was set at 0.9 volts.

In the next place, various experiments were conducted in order to evaluate the effectiveness of activating the sensor cells by supplying them with the alternate treating voltage that was set in accordance with the criteria set forth above, as well as to identify the advantageous conditions for the treatment. The experiments conducted for these purposes will be described below.

In the first experiment, two A/F ratio sensors of the type shown in FIG. 1 were mounted on the exhaust pipe in an internal combustion engine and operated for an extended period so as to elevate the internal resistance of the electromotive force generating cell 5 in each sensor. Thereafter, the sensors were activated in atmospheric air by the method of the present invention. As FIGS. 3a and 3b show, the internal resistance of the cell 5 in each sensor could be lowered.

Figure 3A:
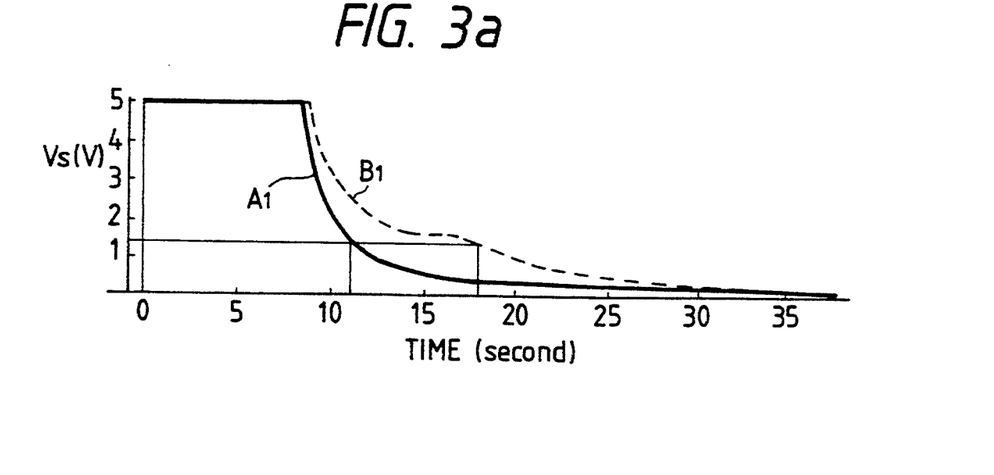
FIGS. 3a and 3b are graphs showing typical desirable effects that are attained by performing an activation treatment on the A/F ratio sensor of FIG. 1 in accordance with the present invention.
Figure 3B:
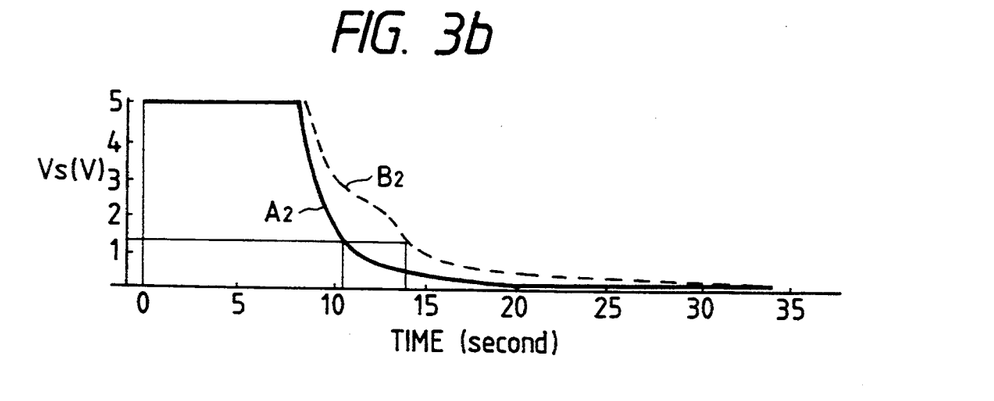

The waveforms A1 and A2 indicated by solid lines in FIGS. 3a and 3b, respectively, show the results of measurement of the change in voltage Vs of the cell 5 that occured under the following conditions: pulse signals (see FIG. 4) with a treating voltage amplitude of $\pm 1.5$ V and a frequency of 0.0083 Hz were applied between the electrodes 13 and 14 of the cell 5 in atmospheric air through three consecutive cycles for 6 min at a treating temperature of 650° C., thereby activating the cell 5 and, subsequently, the heater was energized, whereupon a constant current of 27.5 $\mu A$ was immediately flown into the cell 5 to measure the change in Vs. The waveforms B1 and B2 indicated by broken lines show the results of measurement of the change in Vs of the cell 5 that occurred when a constant current of 27.5 $\mu A$ was flown into the cell 5 before activation as soon as the heater was energized.

The results of these measurements show the following: in the activated A/F ratio sensor, the internal resistance of the cell 5 decreased smoothly as the temperature rose in response to the energization of the heater and, in addition, the drop in resistance was sharp; on the other hand, in the sensor before activation, the internal resistance of the cell 5 decreased only slowly as the temperature rose in response to the energization of the heater and the decrease in resistance was not smooth, producing two apparent droops; in addition, there was a sample-to-sample variation.

In the experiment reported above, the activation treatment was conducted by supplying the cell 5 with pulse signals in which the ratio of the duration of the $+1.5$ V peak to the duration of the $-1.5$ V peak was 1:1. However, another run of experiment showed that this time ratio need not be set at 1:1 but that equally good results could be achieved with other ratios, such as 3:10.

Therefore, in the case of the cell 5 in an A/F ratio sensor of the type contemplated in the embodiment under discussion, one can perform the activation treatment by holding the oxygen partial pressure constant within the internal oxygen reference compartment 17, with the current being allowed to flow for a longer time in such a direction that oxygen would be transported from the diffusing compartment 15 toward the internal reference oxygen compartment 17. If this approach is taken, even if the activation treatment is performed periodically during the execution of A/F ratio control, the sensor can detect the A/F ratio as soon as the treatment ends; in order words, the stop time of A/F ratio control due to the performance of the activation treatment can be shortened.

The second experiment was conducted in order to set the appropriate ranges for temperature, treating voltage and other conditions for the performance of the activation treatment. To this end, a number of samples of the shape shown in FIG. 5 were prepared by a process that comprised screen-printing a Pt electrode on both sides of a green sheet of partially stablized zirconia with a thickness of 0.5 mm and then firing the assembly at 1,525° C. for 1 h in atmospheric air. The thus prepared samples were activated under various conditions and the results were evaluated as follows. The electrodes 21 on each sample measured 2 mm×4 mm.

Figure 5:
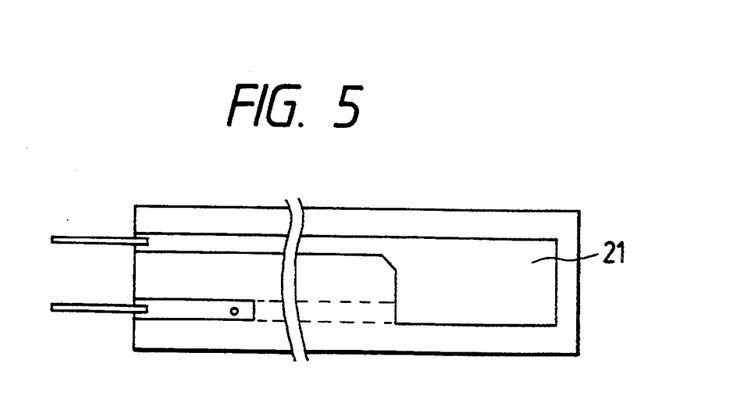
FIG. 5 is a perspective view of the sample that was used in the experiment conducted to set the appropriate ranges for the conditions for the performance of the activation treatment.

In the first run of the experiment, a plurality of samples were charged into furnaces (in atmospheric air) at varying temperatures from 400° C. to 850° C., and each sample was activated by applying pulse signals (amplitude, ±1.5 V; frequency, 0.0083 Hz) between electrodes through 3 cycles for 6 min. Thereafter, the samples treated at different temperatures were supplied with a voltage of 1.5 V between electrodes at 800° C. in atmospheric air, and the resulting current flow was measured to evaluate the effectiveness of the activation.

Figure 6:
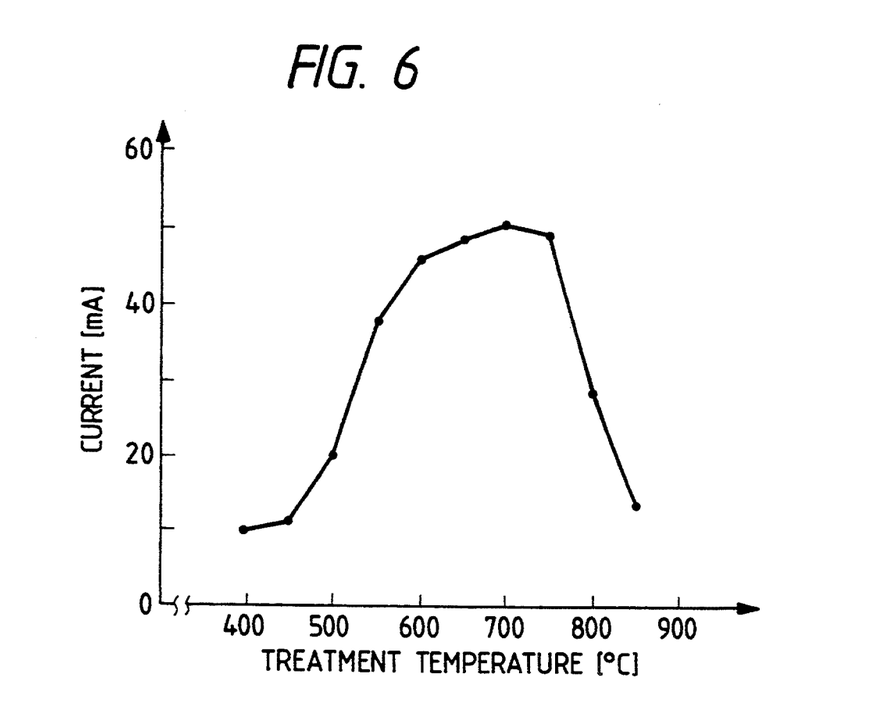
FIG. 6 is a graph showing the result of measurement that was conducted to set the appropriate temperature range for the activation treatment.

The results of the measurement are shown in FIG. 6, from which one can see that a comparatively large current flowed at activation temperatures in the range from 550° C. to 750° C. whereas an extremely small current flowed at temperatures either below 550° C. or above 750° C., with the difference being by a factor of 4 to 6 times. It is therefore clear that the activation treatment is effective if it is conducted within the temperature range from 500° C. to 800° C., preferably from 550° C. to 750° C.

In the second run of the experiment, another group of samples were charged into a furnace at 650° C. (in atmospheric air) and activated by applying pulse signals between electrodes, with the treating voltage amplitude being set at varying values from ±0.1 V to ±2.0 V. As in the first run, the frequency of the applied pulse signals was 0.0083 Hz and the activation treatment was continued through 3 cycles for 6 min. The results are shown in FIG. 7.

Figure 7:
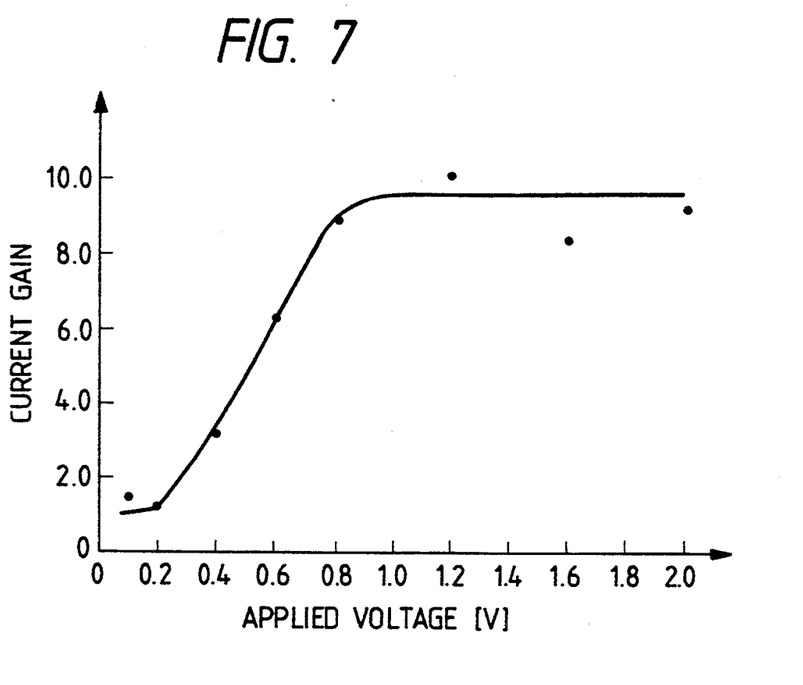
FIG. 7 is a graph showing the result of measurement that was conducted to set the appropriate range for the treating voltage.

The vertical axis of FIG. 7 indicates the current gain by the activation treatment, namely, the ratio of the current flowing after the end of the 3 cycle×6 min treatment to the initial current. As one can see from FIG. 7, the saturation current increased markedly from the initial value when the treating voltage was 0.6 V and above; however, below 0.6 V, there was no significant increase from the initial value, which tendency was pronounced below 0.4 V. It is therefore clear that in order to attain satisfactory results, the treating voltage need be set at 0.4 V and above, preferably at 0.6 V above.

In the third run of the experiment, another samples were charged into a furnace at 650° C. (in atmospheric air) and activated by applying pulse signals between electrodes at varying frequencies from 0.0083 Hz to 10 Hz. The treating voltage was ±1.5 V and the activation time was 6 min. The results are shown in FIG. 8.

Figure 8:
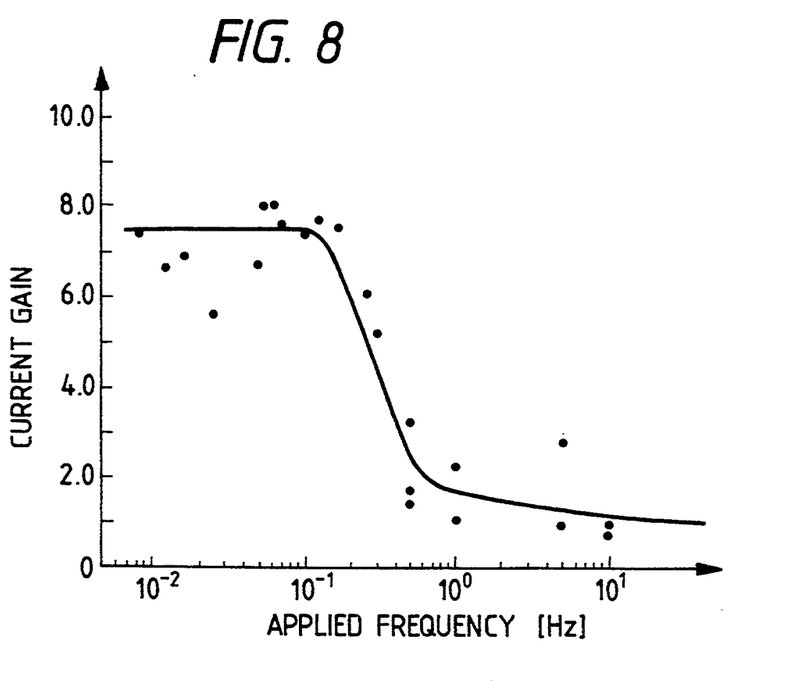
FIG. 8 is a graph showing the result of measurement that was conducted to set the appropriate range for the frequency of the treating voltage.

As in FIG. 7, the vertical axis of the FIG. 8 indicates the current gain by the activation treatment, namely, the ratio of the current flowing after the end of the 6 min treatment to the initial current. As one can see from FIG. 8, the treatment was effective when the frequency of the treating voltage was 0.5 Hz and below and the effect was particularly great at 0.2 Hz and below. It is therefore clear that the frequency of the treating voltage need be set at 0.5 Hz and below, preferably at 0.2 Hz and below.

Figure 4:
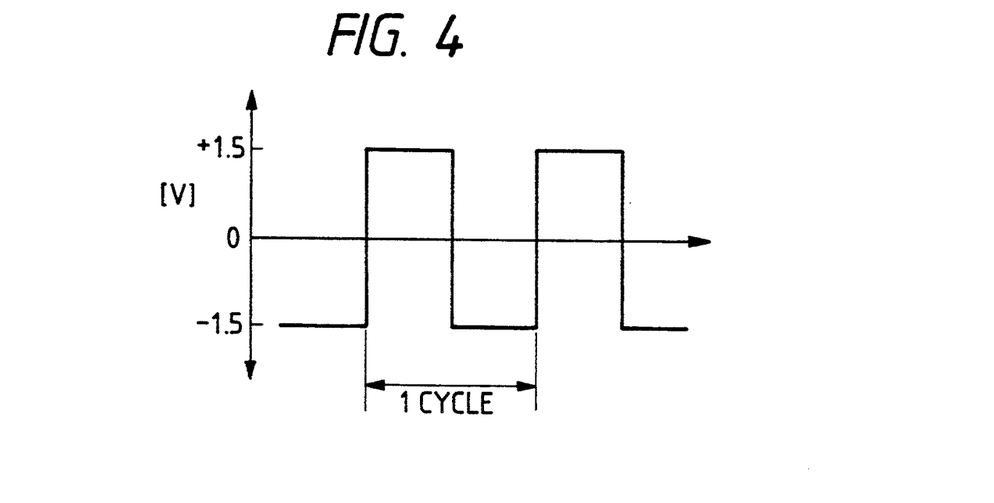
FIG. 4 is a diagram illustrating the waveform of the treating voltage that was applied when performing the activation treatment on the A/F ratio sensor of FIG. 1.

In the fourth run of the experiment, another group of samples were charged into a furnace at 650° C. (in atmospheric air) and activated by applying four kinds of pulse signals (0.008 Hz, 0.016 Hz, 0.05 Hz and 0.5 H) at a treating voltage amplitude of ±1.5 V. In order to investigate the relationship between the number of cycles of pulse application (i.e., the activation time) with the effectiveness of the treatment, the number of pulse application cycles (as FIG. 4 shows, one cycle starts with a first rise of the treating voltage and ends with a second rise) was changed from one to two, three and so one. The results are shown in FIG. 9.

Figure 9:
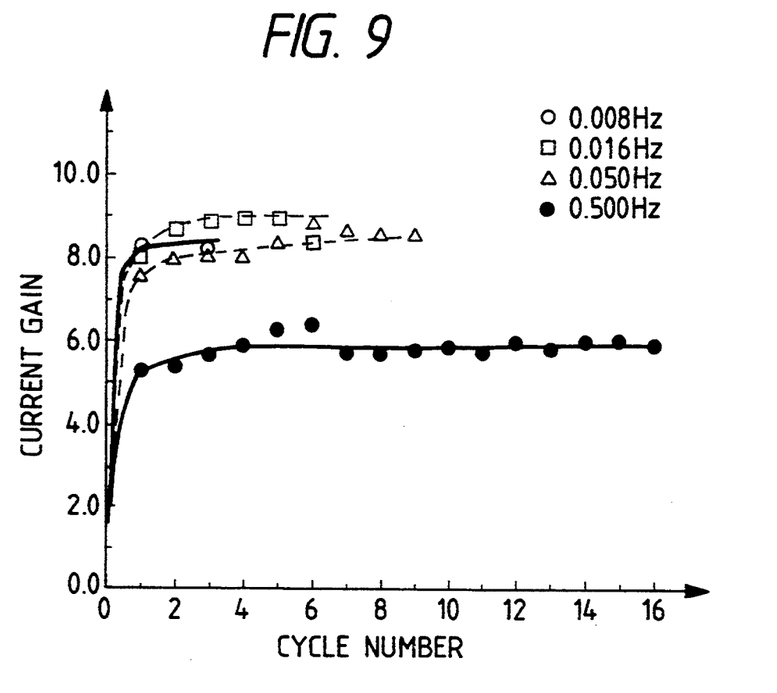
FIG. 9 is a graph showing the result of measurement that was conducted to set the appropriate cycle range for the activation treatment.

As in FIGS. 7 and 8, the vertical axis of FIG. 9 indicates the current gain by the activation treatment, namely, the ratio of the current flowing after the end of the 6 min treatment to the initial current. As one can see from FIG. 9, the activation treatment produced the desired effect at any of the test frequencies when the treating voltage was applied through one or more cycles and the effect was more or less stable after three or more cycles. It is therefore clear that the period of performance of the activation treatment need be set to at least one cycle, preferably at least three cycles, of the treating voltage.

Figure 10:
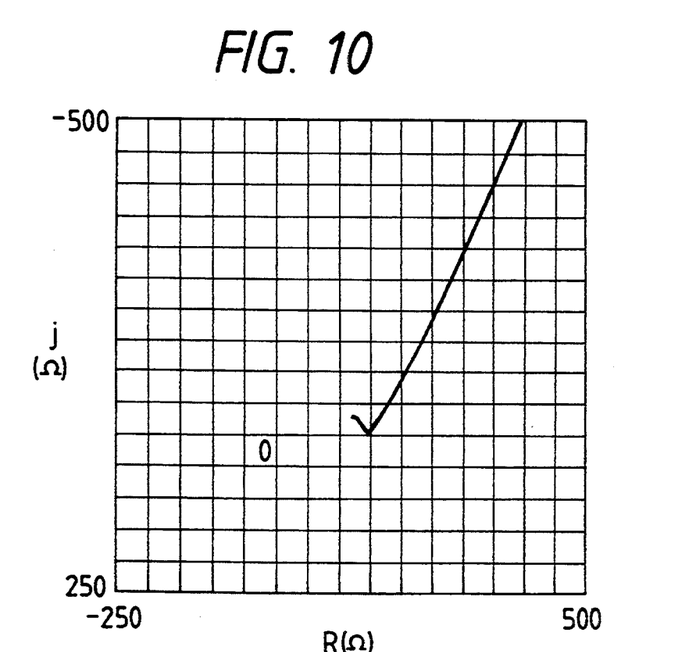
FIG. 10 is a complex impedance plot for a not-activated sample as measured at 650° C.
Figure 11:
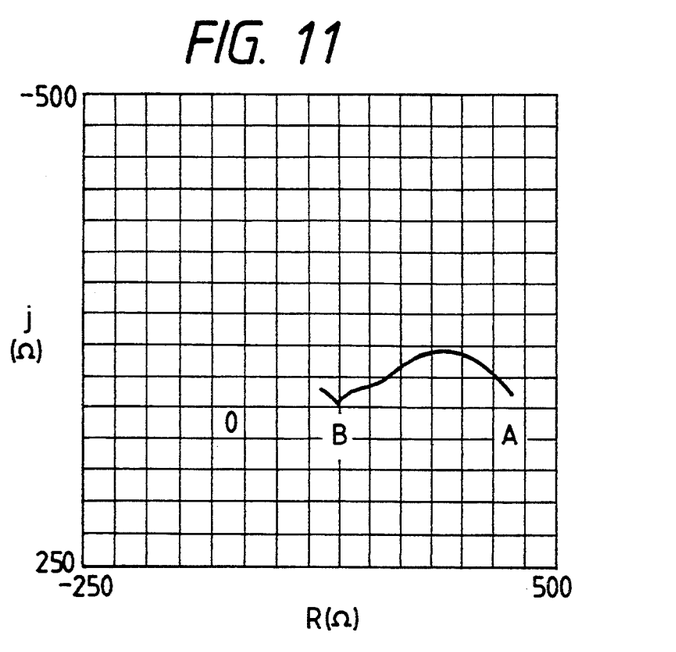
FIG. 11 is a complex impedance plot for an activated sample as measured at 650° C.
Figure 12:
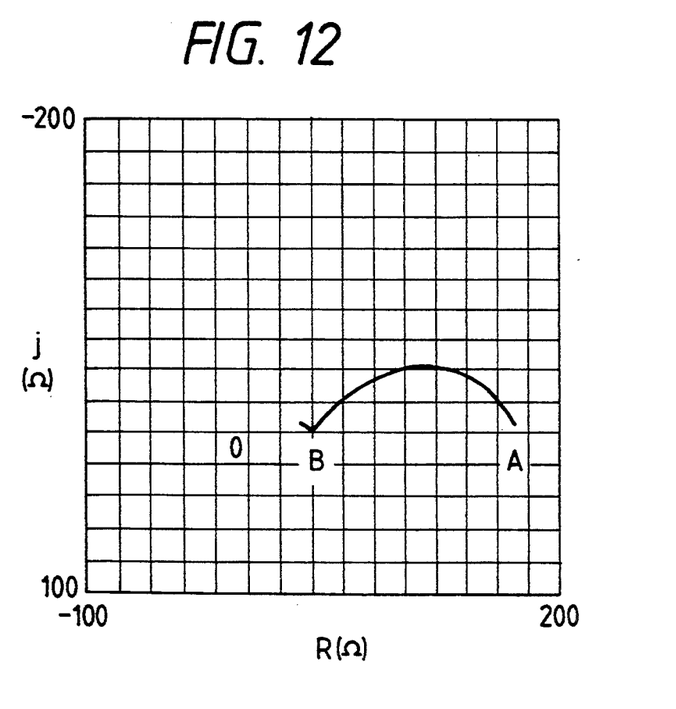
FIG. 12 is a complex impedance plot for a not-activated sample as measured at 800° C.
Figure 13:
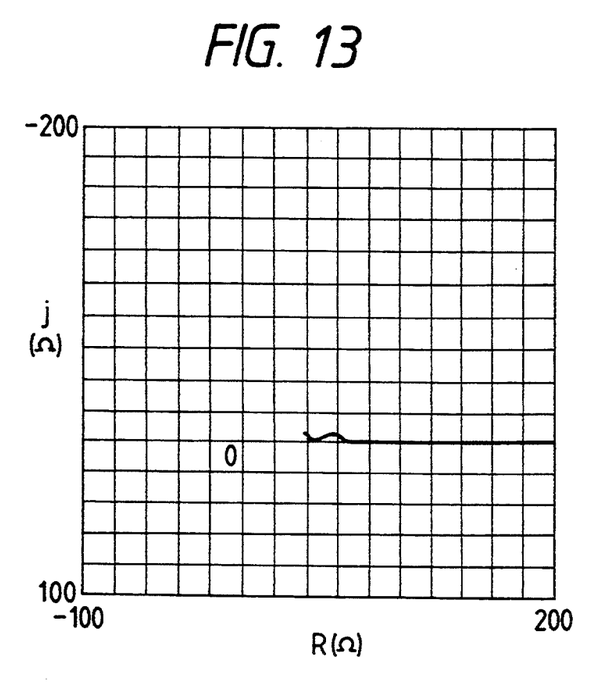
FIG. 13 is a complex impedance plot for an activated sample as measured at 800° C.

In the third experiment, impedance of an activated sample and an untreated sample were measured by a known complex impedance method and the results are shown as complex impedance plots (plot indicating the change of complex impedance due to frequency) in FIGS. 10 to 13. FIG. 10 is a complex impedance plot for the untreated sample as measured at 650° C.; FIG. 11 is a complex impedance plot for the activated sample at 650° C.; FIG. 12 is a complex impedance plot for the untreated sample at 800° C.; and FIG. 13 is a plot for the activated sample at 800° C.

Sample activation was conducted by the following method: the electrodes 21 (see FIG. 5) of the sample were inserted into a furnace at 650° C. (in atmospheric air) and pulse signals having an amplitude of ±1.5 V and a frequency of 0.008 Hz were applied between the electrodes for 6 min. The conditions for conducting the complex impedance measurement were common to all samples except for temperature: frequency range=65 kHz to 0.1 Hz; peak voltage value=100 mV.

Comparison of the results of measurement at 650° C. (FIGS. 10 and 11) shows the following. The resistance of the untreated sample scaled out at the lower frequency end (FIG. 10) and, hence, one may estimate that the untreated sample would have an internal resistance of several kΩ. In contrast, the activated sample had a resistance of about 430 Ω at the lower frequency end (point A in FIG. 11) and a resistance of 140 Ω at the higher frequency end (point B). By subtracting 140 from 430, one may estimate that about 290 Ω would account for the resistance at the interface between each Pt electrode and the solid electrolyte.

Comparison of the results of measurement at 800° C. (FIGS. 12 and 13) shows the following. The untreated sample had a resistance of about 170 Ω at the lower frequency end (point A in FIG. 12) and a resistance of about 40 Ω at the higher frequency end (point B) and, hence, one may estimate that about 130 Ω would account for the resistance at the interface between each Pt electrode and the solid electrolyte. In contrast, the activated sample had a resistance of about 65 Ω at the lower frequency end and a resistance of 40 Ω at the higher frequency end. By subtracting 40 from 65, one may estimate that about 25 Ω would account for the resistance at the interface between each Pt electrode and the solid electrolyte.

Thus, at each temperature of the measurement, the resistance component for the interface between Pt electrode and the solid electrolyte dropped markedly as a result of the activation treatment and this shows that the activation treatment under consideration is effective in lowering the internal resistance of the sensing element.

The foregoing experiments on samples of the type shown in FIG. 5 demonstrate that when performing the activation treatment in atmospheric air, the following conditions will provide satisfactory results: the temperature range from 500° C. to 800° C., preferably from 550° C. to 750° C.; the lower limit of the treating voltage is 0.4 V, preferably 0.6 V; the frequency of the treating voltage is 0.5 Hz or less, preferably 0.2 Hz or less; the treating voltage is applied through one or more cycles, preferably three or more cycles. The frequency of the treating voltage need be 0.5 Hz and less but if its period is unduly long, the activation treatment tends to become less effective; therefore, the frequency of the treating voltage is preferably adjusted to at least 0.0083 Hz which is the smallest of the values tested in the reported experiments.

The foregoing experiments were conducted in atmospheric air using samples of the type shown in FIG. 5 with both electrodes open to the ambient air. However, the A/F ratio sensor shown in FIG. 1 is of such a type that one of the electrodes of each of the sensor cells 3 and 5 is positioned to face the diffusing compartment 15 which communicates with the ambient atmosphere via the diffusion limiting portion or the internal reference oxygen compartment 17. In addition, this sensor is also intended to perform activation treatment during the operation of an internal combustion engine after it is mounted on the exhaust pipe of the engine.

Hence, in order to verify that the activation treatment in accordance with the present invention is effective on the A/F ratio sensor of FIG. 1 not only in atmospheric air but also in an atmosphere equivalent to the exhaust from an internal combustion engine running with a fuel-rich air-fuel mixture, the following experiments were conducted.

In the first run, an alternating voltage having an amplitude of ±1.5 V and a frequency of 0.0083 Hz was applied to each of the sensor cells 3 and 5 for 6 min in atmospheric air while, at the same time, energization of the heater 7 was controlled to heat the pump cell 3 at varying temperatures. Thus, the relationship between the temperature of the activation treatment and its effectiveness in atmospheric air was investigated. In the second run of the experiments, an alternating voltage having an amplitude of ±0.9 V and a frequency of 0.0083 Hz was applied to each of the sensor cells 3 and 5 for 6 min in an atmosphere equivalent to the exhaust from an internal combustion engine running with an air-fuel mixture having an A/F ratio of 12.0 ($C_3H_8+N_2+CO+CO_2+H_2+H_2O$) while, at the same time, energization of the heater 7 was controlled to heat the pump cell 3 at varying temperatures. Thus the relationship between the temperature of the activation treatment and its effectiveness in the fuel-rich atmosphere was investigated. The results of the experiments are shown in Table 1 below, in which the indicated data refer to those on the pump cell 3.

TABLE 1

Treatment Temperature and Its Effectiveness/Pump Cell

| Temperature (°C.) | Initial resistance (Ω) | Resistance after activation (Ω) | Change in resistance (%) |
|---|---|---|---|
| (in atmospheric air with voltage of 1.5 V) | | | |
| 400 | 98.3 | 94.3 | 4.07 |
| 500 | 97.3 | 94.3 | 3.08 |
| 520 | 108.0 | 100.2 | 7.22 |
| 500 | 94.0 | 74.0 | 21.28 |
| 600 | 101.0 | 68.0 | 32.67 |
| 700 | 119.0 | 87.0 | 26.89 |
| 800 | 92.0 | 84.0 | 8.70 |
| 900 | 98.0 | 94.0 | 4.08 |
| (in fuel-rich atmosphere with voltage of 0.9 V) | | | |
| 600 | 249.0 | 229.5 | 7.83 |
| 700 | 240.0 | 210.0 | 12.50 |
| 800 | 233.0 | 201.2 | 13.67 |
| 900 | 238.6 | 222.8 | 6.61 |

In the third run of the experiments, the relationship between the voltage for the activation treatment and its effectiveness was investigated for both atmospheric air and fuel-rich atmosphere by repeating the first and second runs except that the temperature of the sensor cells 3 and 5 was fixed at 700° C. and that the treating voltage was set at varying values. The results of the experiments are shown in Table 2 below.

TABLE 2

Treatment Voltage and Its Effectiveness/Pump Cell

| Voltage (V) | Initial resistance (Ω) | Resistance after activation (Ω) | Change in resistance (%) | Current (mA) | Electromotive force (V) |
|---|---|---|---|---|---|
| (in atmospheric air at 700° C.) | | | | | |
| 0.8 | 123.0 | 92.2 | 25.04 | 4.8 | 0.36 |
| 1.0 | 126.0 | 92.6 | 26.51 | 5.4 | 0.50 |
| 1.2 | 106.8 | 79.6 | 25.47 | 6.0 | 0.72 |
| 1.3 | 112.3 | 85.6 | 23.78 | 6.0 | 0.79 |
| 1.5 | 119.0 | 87.0 | 26.89 | 6.0 | 0.98 |
| 1.7 | 131.2 | 97.4 | 25.76 | 6.0 | 1.12 |
| 2.0 | 129.0 | 96.0 | 25.58 | 7.2 | 1.31 |
| (in fuel-rich atmosphere at 700° C.) | | | | | |
| 0.3 | 257.6 | 239.2 | 1.12 | 1.0 | 0.06 |
| 0.5 | 275.3 | 261.2 | 5.11 | 1.2 | 0.19 |
| 0.7 | 306.5 | 283.2 | 7.60 | 1.7 | 0.22 |
| 0.9 | 240.0 | 210.0 | 12.50 | 2.0 | 0.45 |
| 1.1 | 245.2 | 232.2 | 5.30 | 2.0 | 0.64 |

Notes:
"Current" refers to a minimum current value that caused oxygen to be pumped out of the diffusing compartment. Thus, it is understood that the oxygen partial pressure at the three-phase interface during the treatment was higher than the critical oxygen partial pressure value in both atmospheric air and fuel-rich atmosphere.

Treatment Voltage and Its Effectiveness/Electromotive Cell
(in atmospheric air at 700° C.)

| Voltage (V) | Initial resistance (Ω) | Resistance after activation (Ω) | Change in resistance (%) | Current (mA) | Electromotive force (V) |
|---|---|---|---|---|---|
| 0.8 | 109.8 | 96.6 | 12.02 | 0 | 0.8 |
| 1.0 | 97.4 | 85.8 | 11.91 | 0 | 1.0 |
| 1.2 | 101.6 | 88.4 | 12.99 | 0 | 1.2 |

TABLE 2-continued

| 1.5 | 108.8 | 95.6 | 12.13 | 0 | 1.5 |

Note:
"Current" refers to a minimum value of a current that caused oxygen to be pumped out of the internal reference oxygen compartment. The oxygen partial pressure at the three-phase interface was higher than the critical oxygen partial pressure value.

As is clear from Tables 1 and 2, the results of the foregoing experiments show the following:

As is clear from Tables 1 and 2, the results of the foregoing experiments show the following:

(1) The activation treatment in the fuel-rich atmosphere produced the intended result and successfully lowered the internal resistances of sensor cells 3 and 5; however, compared to the activation treatment in atmospheric air, the percent changes in the internal resistance of pump cell 3 were small, indicating the lower effectiveness of the treatment.

(2) The activation treatment in atmospheric air proved to be effective over the temperature range that was generally the same as in the result of measurements on samples of the type shown in FIG. 5; however, in the fuel-rich atmosphere, satisfactory results could only be attained over a narrow temperature range.

The foregoing description of the preferred embodiment of the present invention concerns a method of activating an A/F ratio sensor and it may be summarized as follows: the critical electromotive force which caused zirconia to blacken in atmospheric air was measured with the measuring element 30; on the basis of the measured value of the critical electromotive force, the treating voltage to be applied when performing the activation treatment in atmospheric air was set; further, on the basis of the critical electromotive force for atmospheric air, the critical oxygen concentration was determined and the critical electromotive force in the fuel-rich atmosphere was computed; and on the basis of the result of this computation, the treating voltage to be applied when performing the activation treatment during the operation of an internal combustion engine was set. By means of these procedures, the internal resistances of sensor cells 3 and 5 could be lowered without causing blackening whether the treatment was performed in atmospheric air or during engine operation. It should be noted that using the measuring element 30 is not absolutely necessary for setting the treating voltage. If desired, a sample of the type shown in FIG. 5 may be prepared and a specified dc voltage may be applied between the electrodes at opposite ends of the sample for a certain period, say, 3 h in the same atmosphere as for the activation treatment, whereby the critical voltage beyond which blackening will occur in zirconia is measured and a voltage equal to or lower than that critical level is set as the treating voltage to be applied for the activation treatment. This method is also effective in performing the intended activation treatment without causing blackening to occur in sensor cell 3 or 5.

What is claimed is:

1. A method of activating a zirconia oxygen sensor that is equipped with a sensing element which has at least one pair of porous electrodes respectively formed on both sides of a plate of oxygen ion conductive solid zirconia electrolyte, said method comprising the steps of:

preparing a measuring device that has a pair of porous electrodes respectively formed on both sides of a plate of oxygen ion conductive solid zirconia electrolyte, with one of said two electrodes of said measuring device being substantially isolated hermetically from an ambient atmosphere, applying a dc current between said pair of electrodes of said measuring device in a specified atmosphere for a period of time, with said isolated electrode being used a cathode, so as to measure a critical electromotive force generated by said sensing element in said specified atmosphere;

setting an alternating specified treating voltage to be applied between said electrodes of said sensing element on the basis of said thus measured critical electromotive force; and applying said alternating specified treating voltage of such a magnitude that an oxygen partial pressure at an electrode-to-solid electrolyte interface of said sensing element is greater than a critical oxygen partial pressure at which said solid electrolyte blackens, said voltage being applied between said electrodes at a temperature of 500° to 800° C.

2. A method of activating a zirconia oxygen sensor according to claim 1, further comprising the steps of, prior to said applying said alternating specified treating voltage step:

calculating a critical oxygen partial pressure at said cathodic isolated electrode from both said critical electromotive force in said specified atmosphere as measured with said measuring device and an oxygen partial pressure of said specified atmosphere; and setting said alternating specified treating voltage to be applied between said electrodes of said sensing element on the basis of said thus calculated critical oxygen partial pressure.

3. A method of activating a zirconia oxygen sensor according to claim 2 wherein an ambient atmosphere in which said sensing element is to be placed during said activating treatment is atmospheric air or an oxygen containing combustion gas atmosphere that is produced by burning an air-fuel mixture having an air excess factor λ greater than one, said method further comprising, prior to said applying said alternating specified treating voltage step:

calculating an oxygen partial pressure for thermodynamic equilibrium either in said ambient atmosphere or in an atmosphere having a lower oxygen concentration than said ambient atmosphere;

calculating a critical electromotive force using a Nernst equation on the basis of both said thus calculated oxygen partial pressure and said critical oxygen partial pressure; and setting said alternating specified treatment, prior to said applying said alternating specified treating voltage step voltage to be applied between said electrodes of said sensing element on the basis of said thus calculated critical electromotive force.

4. A method of activating a zirconia oxygen sensor according to claim 2 wherein an ambient atmosphere in which said sensing element is to be placed during said activating treatment is an oxygen compound containing combustion gas atmosphere that is produced by burning an air-fuel mixture having an air excess factor λ equal to or smaller than one, said method further comprising, prior to said applying said alternating specified treating voltage step:

calculating an oxygen partial pressure for thermodynamic equilibrium either in said ambient atmosphere or in an atmosphere having a lower oxygen compound concentration than said ambient atmosphere:

calculating a critical electromotive force using a Nernst equation on the basis of both said thus calculated oxygen partial pressure and said critical oxygen partial pressure; and setting said alternating specified treating voltage to be applied between said electrodes of said sensing element on the basis of said thus calculated critical electromotive force.

5. A method of activating a zirconia oxygen sensor according to claim 1, wherein said alternating specified treating voltage to be applied between said electrodes of said sensing element is at least 0.4 volts.

6. A method of activating a zirconia oxygen sensor according to claim 1, wherein said alternating specified treating voltage is applied between said electrodes of said sensing element at a frequency not higher than 0.5 Hz.

7. A method of activating a zirconia oxygen sensor according to claim 1, wherein said activating treatment is performed on said zirconia oxygen sensor during or prior to or after its operation periodically.

* * * * *